(12) United States Patent
Samproni et al.

(10) Patent No.: US 10,690,608 B2
(45) Date of Patent: Jun. 23, 2020

(54) SENSOR ARRAY

(71) Applicant: Siemens Healthcare Diagnostics Inc., Tarrytown, NY (US)

(72) Inventors: Jennifer A. Samproni, Braintree, MA (US); Jeffrey R. Jasperse, Newton, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 222 days.

(21) Appl. No.: 15/978,659

(22) Filed: May 14, 2018

(65) Prior Publication Data

US 2018/0266972 A1  Sep. 20, 2018

Related U.S. Application Data

(62) Division of application No. 14/396,099, filed as application No. PCT/US2013/037695 on Apr. 23, 2013, now abandoned.

(60) Provisional application No. 61/636,840, filed on Apr. 23, 2012.

(51) Int. Cl.
*G01N 27/02* (2006.01)
*H05K 1/18* (2006.01)
*G01N 33/49* (2006.01)

(52) U.S. Cl.
CPC .......... *G01N 27/02* (2013.01); *G01N 33/4915* (2013.01); *H05K 1/189* (2013.01); *A61M 2205/3303* (2013.01); *H05K 2201/051* (2013.01); *H05K 2201/055* (2013.01); *H05K 2201/10151* (2013.01)

(58) Field of Classification Search
CPC ........................... G01N 27/02; G01N 33/4915

USPC ........................................................ 73/61.61
See application file for complete search history.

(56) References Cited

U.S. PATENT DOCUMENTS

| 4,381,011 A | 4/1983 | Somers, 3rd |
| 4,740,207 A | 4/1988 | Kreamer |
| 4,762,135 A | 8/1988 | van der Puije et al. |
| 5,007,926 A | 4/1991 | Derbyshire |
| 5,728,137 A | 3/1998 | Anderson-Fignon |

(Continued)

FOREIGN PATENT DOCUMENTS

| CN | 1856703 A | 11/2006 |
| EP | 0737453 A2 | 10/1996 |

(Continued)

OTHER PUBLICATIONS

International Search Report and Written Opinion of International Application No. PCT/US2013/037695 dated Aug. 12, 2013.

(Continued)

*Primary Examiner* — John Fitzgerald
*Assistant Examiner* — Rodney T Frank

(57) ABSTRACT

A sensor assembly has a substrate with a first surface and a second surface opposite the first surface, at least one analyte sensor positioned on at least one of the first surface and the second surface of the substrate, and at least one electrical contact positioned on the substrate in electrical communication with a corresponding one of the at least one analyte sensor. The substrate is configured to define a tube having an interior surface, and an exterior surface. At least a portion of the first surface of the substrate defines the interior surface of the tube, and the at least one analyte sensor is disposed on at least one of the interior surface and the exterior surface of the tube.

13 Claims, 7 Drawing Sheets

(56) References Cited

U.S. PATENT DOCUMENTS

| | | |
|---|---|---|
| 6,475,639 B2 | 11/2002 | Shahinpoor et al. |
| 9,643,186 B1 | 5/2017 | Ahmad |
| 2002/0130311 A1 | 9/2002 | Lieber et al. |
| 2003/0135971 A1 | 7/2003 | Liberman et al. |
| 2005/0187487 A1 | 8/2005 | Azizkhan et al. |
| 2007/0000776 A1 | 1/2007 | Karube et al. |
| 2007/0132043 A1 | 6/2007 | Bradley et al. |
| 2008/0281290 A1 | 11/2008 | Yodfat et al. |
| 2009/0143651 A1 | 6/2009 | Kallback et al. |
| 2009/0297574 A1 | 12/2009 | Ahn et al. |
| 2010/0010328 A1 | 1/2010 | Nguyen et al. |
| 2011/0054583 A1 | 3/2011 | Litt et al. |
| 2012/0045844 A1 | 2/2012 | Rothberg et al. |

FOREIGN PATENT DOCUMENTS

| | | |
|---|---|---|
| EP | 2778668 A1 | 9/2014 |
| JP | S55154454 A | 12/1980 |
| JP | S59085956 U | 6/1984 |
| JP | S6224140 A | 2/1987 |
| JP | 2004512914 A | 4/2004 |
| JP | 2005233917 A | 9/2005 |
| JP | 2006343349 A | 12/2006 |

OTHER PUBLICATIONS

Chunyan Li, "A Spirally-Rolled Flexible Polymer Tube Integrated with Microsensors and Microfluidic Devices for Multifunctional Smart Microcatheters", Oct. 25, 2007, Doctoral Thesis, The University of Cincinnati, pp. 1-173.

Supplementary European Search Report and Written Opinion of European Application No. EP 13781469 dated Mar. 8, 2016.

European Search Report and Written Opinion of European Application No. EP 17161284.9 dated Apr. 24, 2017.

SENSOR ARRAY

INCORPORATION BY REFERENCE

This is a divisional application of U.S. Ser. No. 14/396,099, filed Oct. 22, 2014 which claims the benefit of US National Stage of International Application No. PCT/US2013/037695, filed Apr. 23, 2013 and claims priority under 35 U.S.C. 119(e) to U.S. Provisional Application No. 61/636,840, filed Apr. 23, 2012. All of the applications are incorporated by reference herein in their entirety.

BACKGROUND OF THE INVENTIVE CONCEPTS

1. Field of the Inventive Concepts

The inventive concepts disclosed and claimed herein relate generally to systems and methods for performing fluid diagnostic testing and, more particularly, but not by way of limitation, to sensor assemblies and methods of making sensor assemblies having electrochemical sensors for simultaneously measuring a plurality of parameters in fluid diagnostic testing using low volume samples.

2. Brief Description of Related Art

Bio-sensor arrays are useful in chemistry and medicine to determine the presence and concentration of a biological analyte. For example, various types of analytical tests related to patient diagnosis and therapy can be performed by analysis of a liquid sample taken from a patient's infections, bodily fluids or abscesses. Bodily fluids commonly tested include urine, blood, plasma, saliva, cerebrospinal fluid, pleural fluid, nasopharyngeal and the like. Blood samples, for example, are routinely analyzed to obtain measurements of the partial pressures of $CO_2$ and $O_2$ and concentrations of electrolytes and metabolites in the blood.

A number of different analyzers currently exist for making such measurements utilizing rigid layered sensor assemblies and electrical circuits. Such sensor assemblies are used to assess the condition of medical patients through primary clinical indications, for example, through monitoring of $pCO_2$, $pO_2$, pH, $Na^+$, $K^+$, $Ca^{2+}$, $Cl^-$, glucose, lactate, and hemoglobin values. Because of the frequency which many patients are tested, the ability to use small sample sizes for performing analysis is desirable. Patients in intensive care units may require a sampling frequency of 15-20 per day for blood gas and clinical chemistry measurements. In these cases, analyzing small blood samples is desirable due to the relatively large number of samples taken in a relatively short period of time. Further, to limit the number of tests performed, it is desirable to gather as much information as possible with each test.

Some prior art analyzers include a sensor array which itself defines one wall of a flow channel. A fluidic path is created using a second material such as molded plastic which is bonded to the wall containing the sensor components. Other bio-sensor assemblies for fluid analysis consist of multiple substrates with an intervening spacer acting to provide a fluid path.

Sensor assemblies utilizing spacers generally have sensors disposed on one or two plate-like surfaces. When joined with the intervening spacer, the two substrates are positioned so that the surfaces of the substrates which support sensors face one another. The intervening spacer may provide and define a substantially straight flow channel for the fluid sample, or may redirect flow from sensor to sensor disposed about the inner surface of the attached substrates. One low volume multi-analyte analyzer uses an adhesive layer with pressure sensitive adhesive (PSA) to provide and define a flow path between two sets of opposing sensors. PSA films are readily applied to rigid substrates.

A problem with the current systems is that in order to reduce sample volume requirements, the flow channel cross-section and/or length must be reduced which, in turn, can limit the sensor membrane cross-section and its total volume. A need exists for an economical bio-sensor array which can increase the number of sensors while maintaining or decreasing sample volume requirements. It is to such an apparatus and method that the inventive concepts disclosed herein are directed.

SUMMARY OF THE INVENTIVE CONCEPTS

The inventive concepts disclosed and claimed herein generally relate to a sensor assembly. The sensor assembly has a substrate with a first surface and a second surface opposite the first surface, at least one analyte sensor positioned on at least one of the first surface and the second surface of the substrate, and at least one electrical contact positioned on the substrate in electrical communication with a corresponding one of the at least one analyte sensor. The substrate is configured to define a tube having an interior surface and an exterior surface. At least a portion of the first surface of the substrate defines the interior surface of the tube, and the at least one analyte sensor is disposed on at least one of the interior surface and the exterior surface of the tube.

BRIEF DESCRIPTION OF THE DRAWINGS

Like reference numerals in the figures represent and refer to the same or similar element or function. Implementations of the disclosure may be better understood when consideration is given to the following detailed description thereof. Such description makes reference to the annexed pictorial illustrations, schematics, graphs, and drawings. The figures are not necessarily the scale and certain features and certain views of the figures may be shown exaggerated, to scale or in schematic in the interest of clarity and conciseness. In the drawings.

DETAILED DESCRIPTION OF EXEMPLARY EMBODIMENTS

Figure 1:
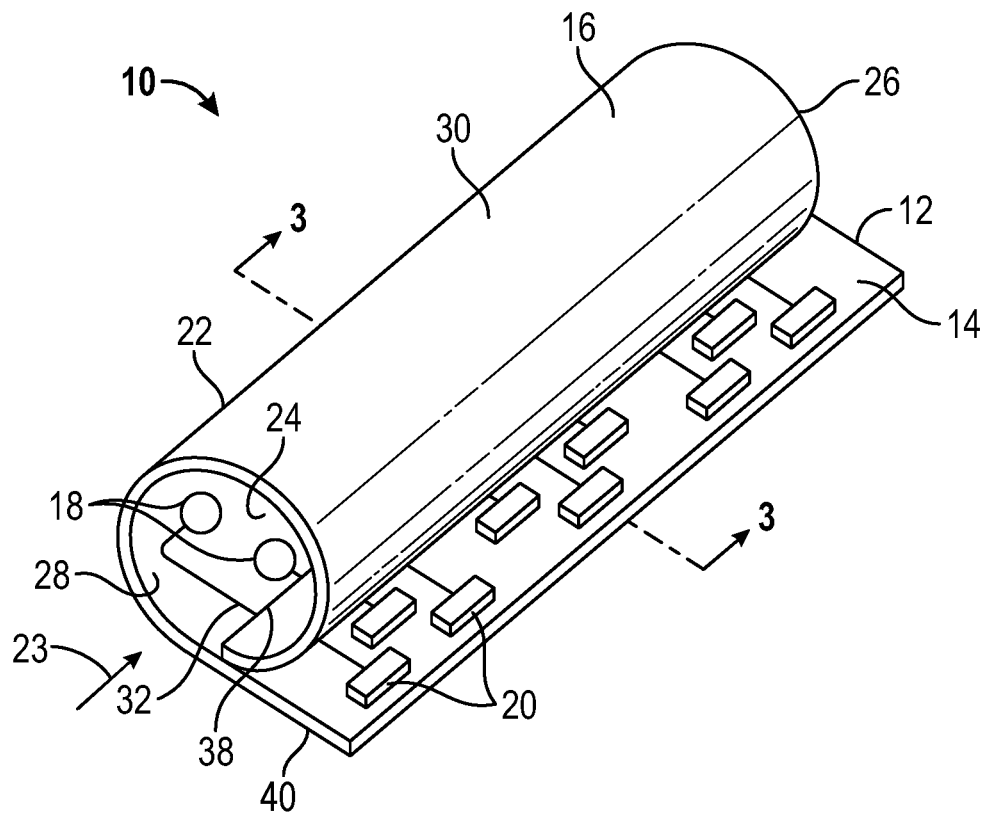
FIG. 1 is a perspective view of a sensor assembly constructed in accordance with the inventive concepts disclosed herein.

Before explaining at least one embodiment of the inventive concepts disclosed herein in detail, it is to be understood that the inventive concepts are not limited in their application to the details of construction, experiments, exemplary data, and/or the arrangement of the components set forth in the following description, or illustrated in the drawings. The presently disclosed and claimed inventive concepts are capable of other embodiments or of being practiced or carried out in various ways. Also, it is to be understood that the phraseology and terminology employed herein is for purpose of description only and should not be regarded as limiting in any way.

In the following detailed description of embodiments of the inventive concepts, numerous specific details are set forth in order to provide a more thorough understanding of the inventive concepts. However, it will be apparent to one of ordinary skill in the art that the inventive concepts within the disclosure may be practiced without these specific details. In other instances, well-known features have not been described in detail to avoid unnecessarily complicating the instant disclosure.

Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Referring now to the drawings, and more particularly to FIG. 1, shown therein is an exemplary embodiment of a sensor assembly 10 constructed in accordance with the inventive concepts disclosed and claimed herein. The sensor assembly 10 comprises a substrate 12 having a first surface 14 and a second surface 16 opposite the first surface 14. At least one analyte sensor 18 is positioned on the first surface 14 of the substrate 12. At least one electrical contact 20 is positioned on the substrate 12 in electrical communication with a corresponding one of the at least one analyte sensor 18. The substrate 12 is configured to define a tube 22 defining a fluid flow path 23, and having a fluid inlet 24, a fluid outlet 26, an interior surface 28, and an exterior surface 30. At least a portion of the first surface 14 of the substrate 12 defines the interior surface 28 of the tube 22, and the at least one analyte sensor 18 is disposed on the interior surface 28 of the tube 22.

The substrate 12 can be made from a number of materials such as glass, plastic or a ceramic material such as an oxide of aluminum, silicon or boron. Suitable materials are well known to those skilled in the art. In one embodiment, the substrate 12 is a flexible material. Nonlimiting examples of suitable flexible materials include paper, polyethylene terephthalate (PET), polyethylene (PE), polyimide (PI), polyether ether ketone (PEEK), and the like. Use of a flexible substrate can reduce the size and weight of the sensor assembly 10. As discussed in detail in subsequent sections of this disclosure, use of a flexible substrate can allow increased circuit density and economic modification of the overall shape of the sensor assembly 10.

The analyte sensor 18 positioned on the first surface 14 of the substrate 12 can be any sensor capable of measuring a chemical or physical parameter, such as the concentration of a chemical substance. Nonlimiting examples of sensor measurements in blood samples include $pCO_2$, $pO_2$, pH, $Na^+$, $K^+$, $Ca^{2+}$, glucose, lactate, and hemoglobin. Many different types and designs of analyte sensors 18 can be used. Typically, the analyte sensor 18 includes two or three electrodes (not shown). The analyte sensor 18 may be in direct contact with the fluid being measured, and may include a thin membrane or the like providing indirect contact between the fluid and the electrodes in the analyte sensor 18. In one embodiment, the analyte sensor 18 is an electrochemical biosensor and can employ conductivity, potentiometric, or amperometric techniques to convert the chemical information into a measurable signal.

For example, biosensors based on conductivity techniques make use of the fact that electrochemical reactions produce ions or electrons, and the conductivity or resistivity of the solution changes proportionally. Potentiometric biosensors can utilize an ion-selective electrode or an electrode having an ion-permeable membrane that selectively permits the ion of interest to diffuse through. The operating principle is based on the fact that when a voltage is applied to the solution, there is a change in current flow due to electrochemical reactions. Amperometric biosensors have high sensitivity for detecting electro-active species present in biological samples and are often used for analytes such as glucose and lactate. Amperometric biosensors utilize both working and reference electrodes, the working electrode being usually either a noble metal or a screen-printed layer covered by a biorecognition component.

Analyte sensors 18 can now be fabricated in a planar format, for example by successively applying thin layers of materials to a base dielectric substrate using thick-film and/or thin-film techniques. Planar analyte sensors can be made smaller and configured more closely together, reducing the sample volume requirements. Manufacturing of planar thick-film electrodes on ceramic wafers is often done using standard processes. The use of ultrapure metals can be used to prolong use-life under constant polarization. Conductive and dielectric inks have been utilized, such as platinized carbon paste ink for screen-printing the active electrode of a glucose and lactate biosensor. Polymers can be used as an internal electrolyte such as Nafion, a sulfonated tetrafluoroethylene polymer, used as an internal electrolyte in some amperometric sensors for $pO_2$. For ion-selective analyte sensors, a copolymer of methacrylamidopropyltrimethylammonium chloride and methyl methacrylate (MAP-TAC/MMA) has been used as a solid internal contact.

Thus, a wide variety of analyte sensors 18 can be used, alone or in combination, with each analyte sensor 18 being in electrical connection with a corresponding electrical contact 20 positioned on the substrate 12. In one embodiment, components of the analyte sensor 18, as well as the electrical contact 20, utilize materials and methods recently developed and understood by those skilled in the art, enabling circuits to be printed onto a flexible substrate such as a flexible polymer sheet. Such printed circuits are commonly referred to as flex circuits. While known materials and methods of making flexible circuits are described herein, it is understood that new and presently unknown materials for making and fixing the analyte sensor 18 and the electrical contact 20 onto a flexible substrate are also to be included in the presently disclosed and claimed inventive concepts.

Design and manufacture of the sensor assembly 10 with a flexible substrate can include single-sided, double access, and double-sided flex circuits. Single-sided flex circuits have a single conductor layer made of either a metal or conductive (metal filled) polymer on a flexible dielectric film. Component termination features are accessible from one side. Holes may be formed in the base film to allow component leads to pass through for interconnection. Single sided flex circuits can be fabricated with or without such protective coatings as cover layers or cover coats. Double access flex circuits have a single conductor layer which is processed so as to allow access to selected features of the conductor pattern from both sides. Double-sided flex circuits actually have two conductor layers.

Polymer thick film flex circuits can be manufactured using identical components as used for rigid printed circuit boards, allowing the board to conform to a desired shape, or to flex during its use. Flex circuits are often made with a photolithographic technology. An alternative way of making flexible foil circuits includes laminating very thin copper strips in between two layers of PET. These PET layers are coated with an adhesive which is thermosetting, and will be activated during the lamination process.

In one embodiment, conductive inks and dielectric inks are deposited onto the substrate 12 using screen printing, rotogravure, pad printing, stenciling, jetting and the like to provide the electrical contact 20, as well as electrodes and other components of the analyte sensor 18. The conductive ink may be formed in part by nanoparticle platinum, gold, silver, copper, silicon, or any other conductive element or combination of elements. Membrane materials are applied to appropriate areas of the substrate 12 to produce a functioning analyte sensor 18. The substrate 12 is flexible and can be made from paper, polyethylene terephthalate (PET), polyethylene (PE), polyimide (PI), and the like.

The electrical contact 20 in electrical communication with the corresponding analyte sensor 18 can be any shape and any conductive material. Suitable materials for the electrical contact 20 include, but are not limited to, gold, silver, copper and aluminum metals and alloys thereof as well as conductive inks.

Figure 2:
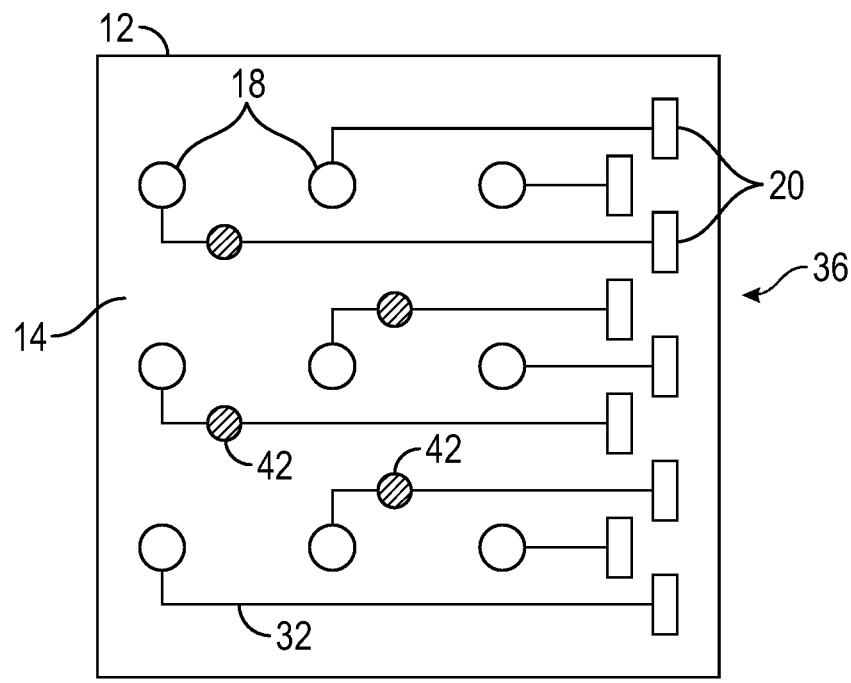
FIG. 2 is a planar view of a portion of a substrate constructed as in FIG. 1.
Figure 3:
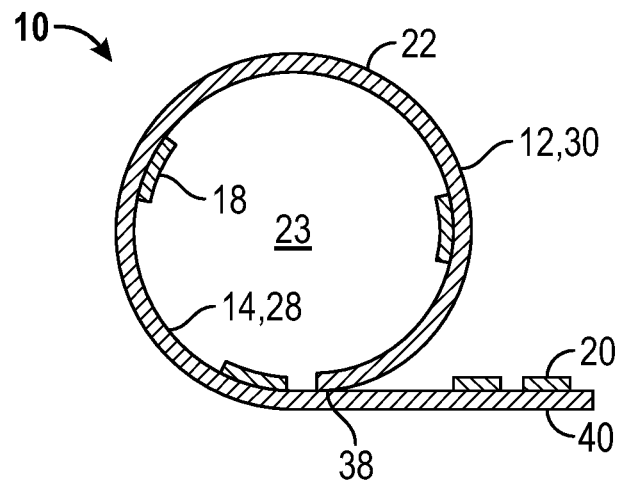
FIG. 3 is a sectional view taken along line 3-3 of FIG. 1.

In one embodiment, the electrical contact(s) 20 is positioned on the first surface 14 of the substrate 12, as exemplified in FIG. 1 through FIG. 3. Electrical communication between the analyte sensor 18 and the electrical contact 20 can be achieved using a trace 32, also positioned along the first surface 14 of the substrate 12. The trace 32 can be a strip of conductive metal such as copper, conductive ink, and the like, capable of making an electrical connection to carry signals between the analyte sensor 18 and the electrical contact 20. The electrical contact 20 is positioned, sized and shaped to mesh with an electrical contact to an analyzer (not shown) for processing and outputting analyte results based on analyte sensor measurements of a fluid sample.

Figure 4:
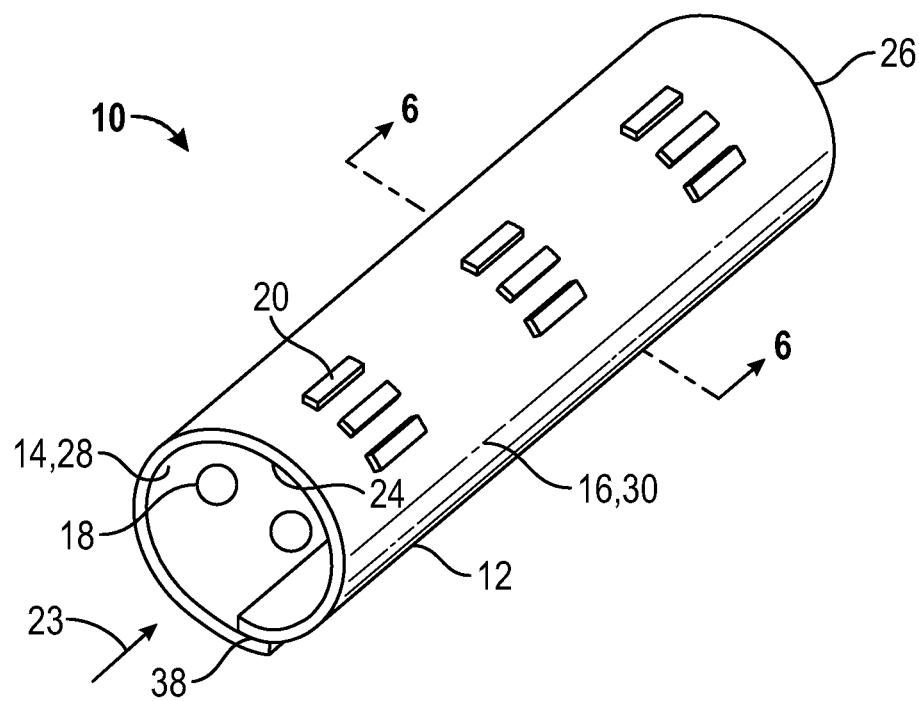
FIG. 4 is a perspective view of another embodiment of a sensor assembly constructed in accordance with the inventive concepts disclosed herein.
Figure 5:
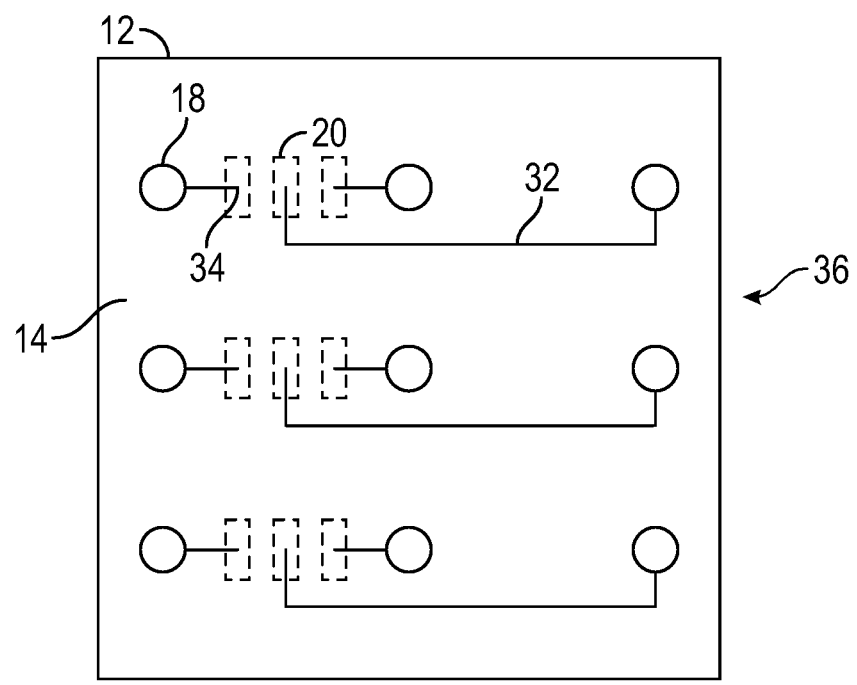
FIG. 5 is a planar view of a portion of a substrate constructed as in FIG. 4.
Figure 6:
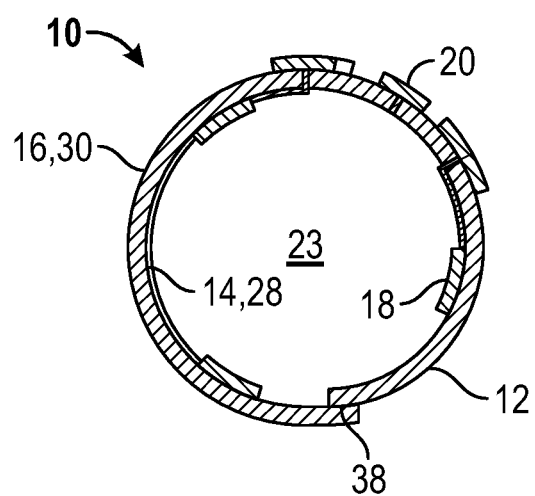
FIG. 6 is a sectional view taken along line 6-6 of FIG. 4.

In another embodiment, the electrical contact(s) 20 is positioned on the second surface 16 of the substrate 12, as exemplified in FIG. 4 through FIG. 6. Electrical communication between the analyte sensor 18 positioned on the first surface 14, and the electrical contact 20 positioned on the second surface 16, can be achieved using a trace 32 which can be partly positioned along the first surface 14 of the substrate 12. The trace 32 passes through a hole or via 34 at some point to connect to the corresponding electrical contact 20 on the second surface 16. The via 34 can be, for example, a bore filled with an electrical conductive material, e.g., a metal or conductive ink.

Figure 7:
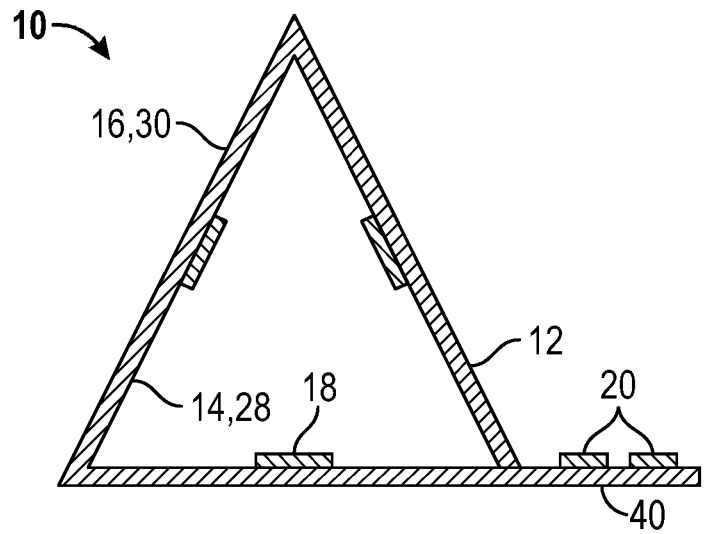
FIG. 7 is a sectional view of an embodiment of the sensor assembly constructed in accordance with the inventive concepts disclosed herein.
Figure 8:
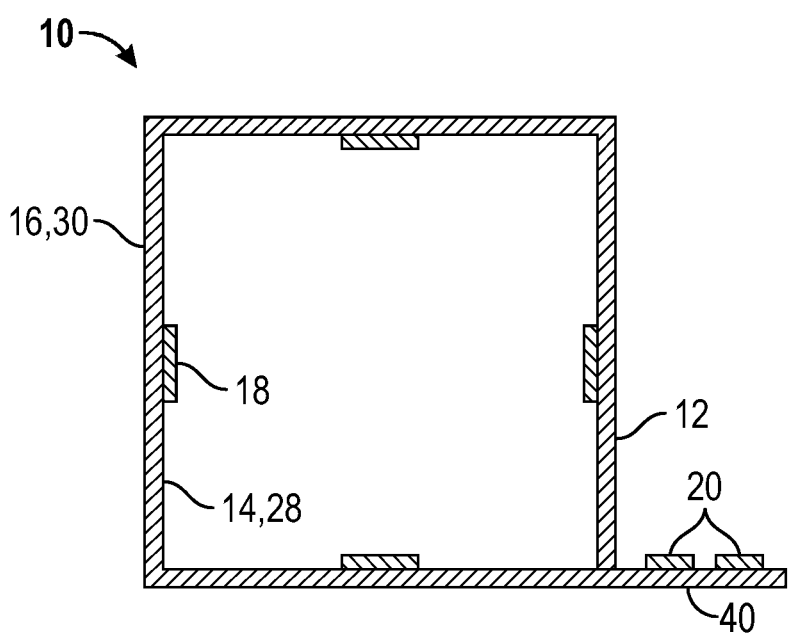
FIG. 8 is a sectional view of another embodiment of the sensor assembly constructed in accordance with the inventive concepts disclosed herein.

The substrate 12 can be configured to define the tube 22 by, for example, rolling, bending or folding the substrate 12 to the desired shape. In one embodiment, the substrate 12, to which has been attached the analyte sensor, electrical contact 20, trace 32, and other necessary or desired electrical components and connections (referred to collectively as "circuit 36") can be planar during application of the circuit 36, and then rolled to form a tube 22 having a circular cross-section as in FIG. 1 through FIG. 6. In another embodiment, the substrate 12 with attached circuit 36 can be bent or folded to form a tube 22 having at least three planar sides as, for example, in FIG. 7 and FIG. 8.

The tube 22 has a fluid inlet 24 and a fluid outlet 26, as well as an interior surface 28 and an exterior surface 30. The sensor assembly 10 can be constructed on a unitary one piece substrate 12, the sensor assembly 10 having only a single seam 38 that can be secured using pressure sensitive adhesive, epoxy, acrylic, or other bonding means and materials known to those skilled in the art. The need for a spacer material is eliminated. Additionally, multiple analyte sensors 18 can be printed onto a film, for example, with sufficient distance between electrodes to minimize cross-talk and other interference. When the substrate 12 and analyte sensors 18 are rolled into a tube configuration, sensor placement becomes both opposing and adjacent, thereby enabling a higher number of analyte sensors 18 in a smaller fluidic path.

In one embodiment, the electrical contact(s) 20 is positioned on the second surface 16 of the substrate 12 as exemplified in FIG. 4 to FIG. 6. The electrical contact(s) 20 can be readily connected to the analyzer using, for example, a receiving portal with an electrical contact(s) configured to mesh with the electrical contact(s) 20 on the outer surface of the tube 22.

In one embodiment, the electrical contact(s) 20 is positioned on the first surface 14 of the substrate 12, as exemplified in FIG. 1 through FIG. 3, FIG. 7 and FIG. 8, and the substrate 12 is rolled, bent or folded to leave a tab 40 extending from the tube 22 and having the electrical contact 20 positioned on the tab 40. The tab 40 can extend in a tangential relationship to the tube 22. The tab 40 can be readily connected to the analyzer using, for example, a ribbon-type connector configured to mesh with the electrical contact(s) 20 and the tab(s) 40 to transfer electrical signals for processing and outputting analyte results based on sensor measurements of a fluid sample.

Referring to FIG. 2, an amplifier front-end circuit 42 can be positioned on the first surface of the substrate proximate to and in electrical communication with a corresponding one of the at least one analyte sensor 18. The amplifier front-end circuit 42 can be useful when the analyte sensor 18 produces a low-range output susceptible to interference and noise. Such interference and noise can corrupt the integrity of a signal transferred along the trace 32. The amplifier front-end circuit 42 amplifies the signal from the analyte sensor 18 before communicating the signal to the analyzer (not shown) for processing and outputting analyte results. The amplification reduces signal loss and improves the risk of corrupting the signal integrity while it is communicated to the analyzer.

As with the analyte sensor 18, the amplifier front-end circuit 42 may be formed by printing, using a conductive ink, directly on the substrate 12, or onto a thin film membrane later applied to the substrate 12. The amplifier front-end circuit 42 is positioned on the substrate 12 in close proximity to the analyte sensor 18 and electrically connected along the trace 32.

Figure 9:
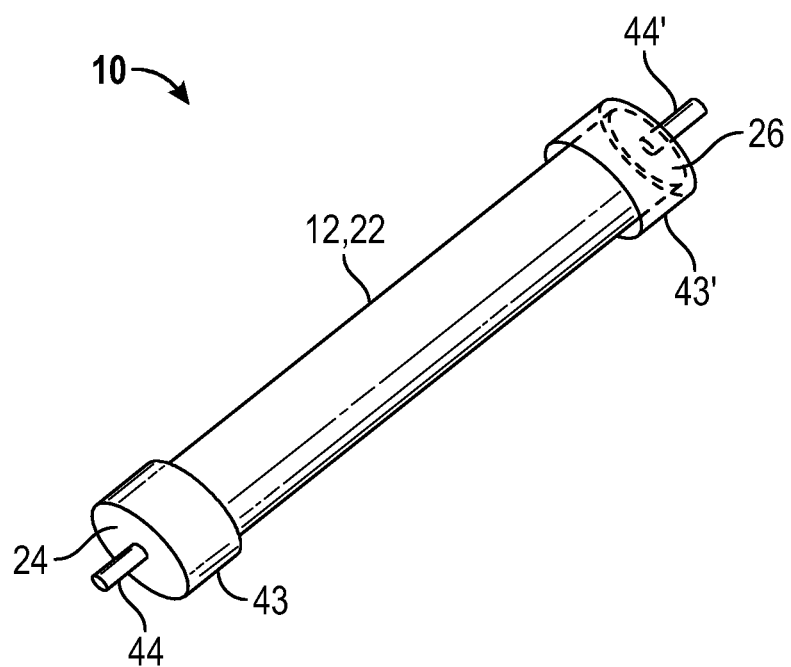
FIG. 9 is a perspective view of a sensor assembly showing caps at either end.

Referring now to FIG. 9, the sensor assembly 10 can include a first cap 43 covering the fluid inlet 24 and/or a second cap 43' covering the fluid outlet 26. The first cap 43 may include a nipple 44 for facilitating insertion of the fluid sample to be analyzed into the tube 22. Similarly, the second cap 43' may include a nipple 44' to facilitate removal of the fluid sample from the tube 22.

Figure 10:
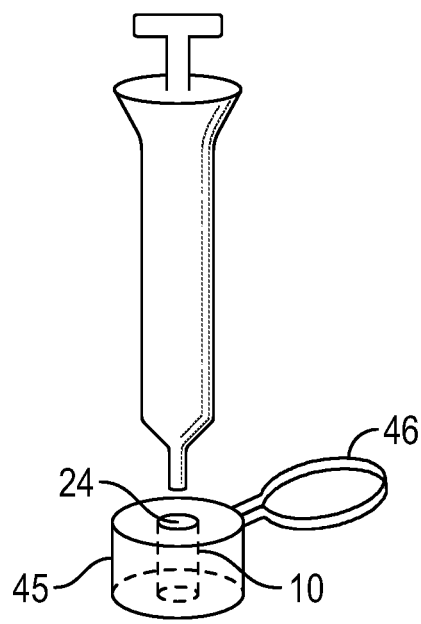
FIG. 10 is a perspective view illustrating delivery of fluid to a sensor assembly.

In one embodiment, the sensor assembly 10 includes a collar 45 and optionally a collar cap 46 as shown in FIG. 10. The collar 45 facilitates manual insertion of a liquid sample into the sensor assembly 10 and is easy to handle and store. The collar 45 also facilitates moving the sensor assembly to and from the analyzer.

Figure 11:
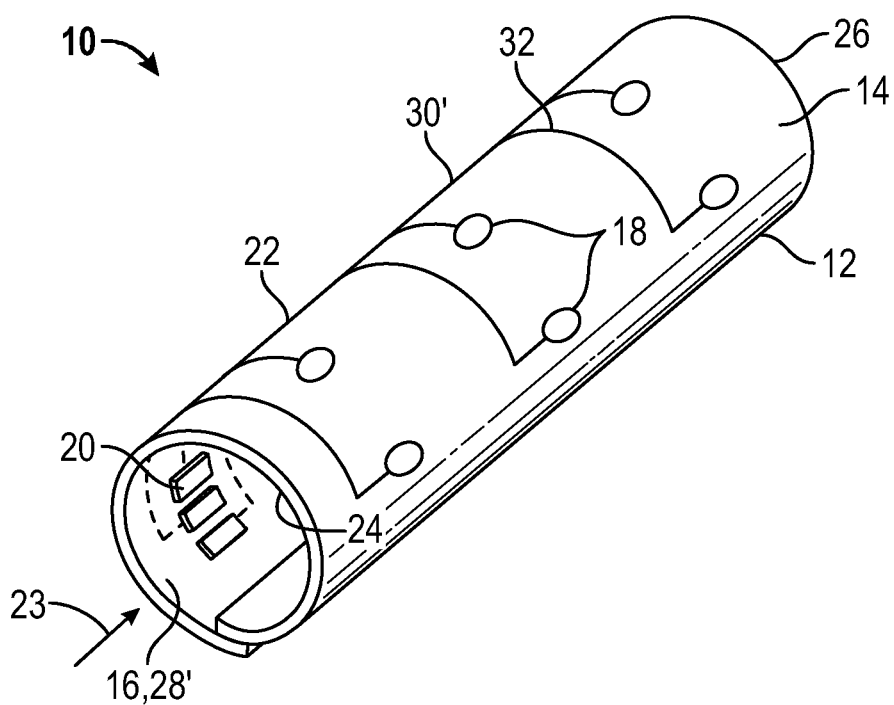
FIG. 11 is a perspective view of another embodiment of a sensor assembly constructed in accordance with the inventive concepts disclosed herein.

Referring now to FIG. 11, shown therein is another exemplary embodiment of a sensor assembly 10 constructed in accordance with the inventive concepts disclosed and claimed herein. In this embodiment, the substrate 12 is configured to define a tube 22 having an interior surface 28', and an exterior surface 30'. At least one analyte sensor 18 is disposed on the exterior surface 30' of the tube 22, while the corresponding electrical contact 20 is positioned on the interior surface 30' of the tube 22. It is contemplated that a sensor assembly 10 with this arrangement could be used as a cannula for inserting into the body for making fluid measurements. Wiring 50 can be housed within the tube 22, and body fluid can be accessed on the exterior surface 30' of the tube.

Figure 12:
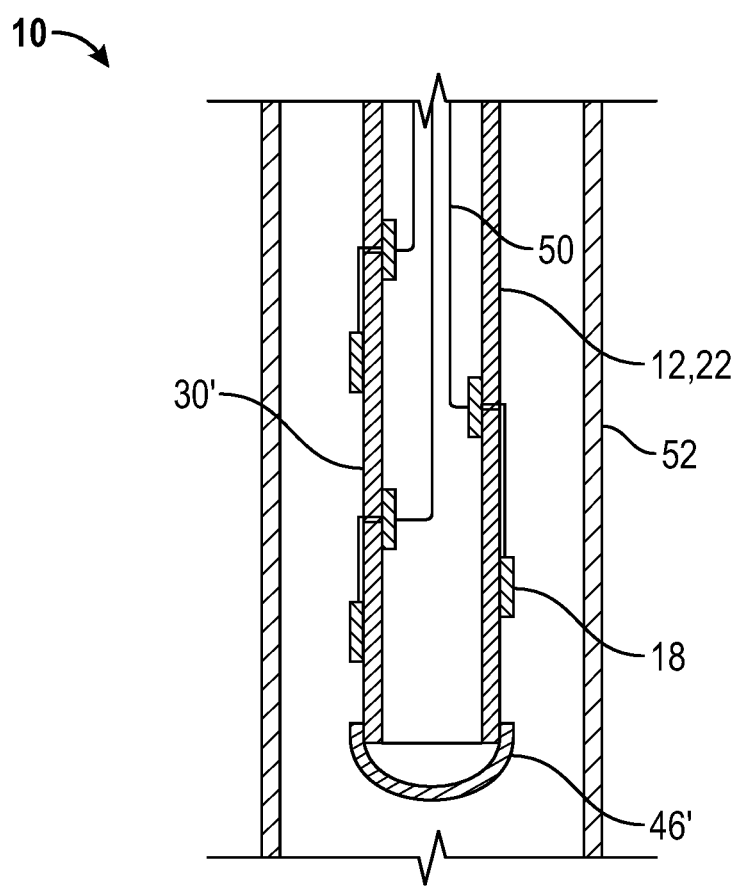
FIG. 12 is a sectional view of yet another embodiment of a sensor assembly constructed in accordance with the inventive concepts disclosed herein.

The embodiment shown in FIG. 11 can also be housed within an outer cannula 52, as shown in FIG. 12, with the tube 22 and the outer cannula 52 defining an annulus 54 therebetween. Blood or other fluid to be monitored flows through the annulus 54 and is measured by the one or more analyte sensor(s) 18. A cap 43' prevents fluid from entering the interior of the tube 22. When used for insertion into a patient's body, the outer cannula 52 is made of material harmless to the human body. This design can be useful in situations where a patient's exposure, or prolonged exposure, to the exterior surface 30' of the tube 22 is undesireable.

A method of forming a sensor assembly includes the step of forming a plurality of analyte sensors on a surface of a flexible substrate, as described above. A plurality of electrical contacts are formed on the flexible substrate such that the electrical contacts are in electrical communication with a corresponding one of the analyte sensors. The flexible substrate is then configured to define a tube having a fluid inlet, a fluid outlet, an interior surface, and an exterior surface with the surface on which the analyte sensors are formed defining the interior surface of the tube such that the analyte sensors are disposed on the interior surface of the tube. If desired, the sensor assembly can be treated chemically or by heat to add rigidity. Optionally, a stiffener can be attached to the sensor assembly to support and maintain the overall shape.

Similarly, another method of forming a sensor assembly includes the steps of forming a plurality of analyte sensors on a surface of a flexible substrate, and forming a plurality of electrical contacts on the flexible substrate such that the electrical contacts are in electrical communication with a corresponding one of the analyte sensors. In this case, the flexible substrate is configured to define a tube having an interior surface and an exterior surface with the surface on which the analyte sensors are formed defining the exterior surface of the tube such that the analyte sensors are disposed on the exterior surface of the tube.

From the above description, it is clear that the inventive concept(s) disclosed herein is well adapted to carry out the objects and to attain the advantages mentioned herein as well as those inherent in the inventive concept disclosed herein. While exemplary embodiments of the inventive concept disclosed herein have been described for purposes of this disclosure, it will be understood that numerous changes may be made which will readily suggest themselves to those skilled in the art and which are accomplished without departing from the scope of the inventive concept disclosed herein and defined by the appended claims.

What is claimed is:

1. A sensor assembly, comprising:
    a substrate having a first surface and a second surface opposite the first surface;
    at least one analyte sensor positioned on at least one of the first surface and the second surface of the substrate; and
    at least one electrical contact positioned on the substrate in electrical communication with a corresponding one of the at least one analyte sensor,
    wherein the substrate is configured to define a tube having an interior surface, and an exterior surface with at least a portion of the first surface of the substrate defining the interior surface of the tube and the at least one analyte sensor disposed on at least one of the interior surface and the exterior surface of the tube,
    wherein the substrate is further configured to have a tab extending from the tube in a tangential relationship to the tube,
    wherein the at least one electrical contact is positioned on the tab.

2. The sensor assembly of claim 1, wherein the substrate is flexible.

3. The sensor assembly of claim 1, wherein the substrate is a one piece substrate.

4. The sensor assembly of claim 1, wherein the tube has a circular cross-section.

5. The sensor assembly of claim 1, wherein the at least one electrical contact is positioned on the exterior surface of the tube.

6. The sensor assembly of claim 1, further comprising:
    at least one amplifier front-end circuit positioned on the substrate proximate to and in electrical communication with a corresponding one of the at least one analyte sensor.

7. A sensor assembly, comprising:
    a substrate having a first surface and a second surface opposite the first surface; at least one analyte sensor positioned on the first surface of the substrate; and at least one electrical contact positioned on the substrate in electrical communication with a corresponding one of the at least one analyte sensor, wherein the substrate is configured to define a tube having an interior surface, and an exterior surface with at least a portion of the second surface of the substrate defining the interior surface of the tube and the at least one analyte sensor disposed on the interior surface of the tube, wherein the substrate is further configured to have a tab extending from the tube in a tangential relationship to the tube, wherein the at least one electrical contact is positioned on the tab.

8. The sensor assembly of claim 7, wherein the substrate is flexible.

9. The sensor assembly of claim 7, wherein the substrate is a one piece substrate.

10. The sensor assembly of claim 7, wherein the tube has a circular cross-section.

11. A method of forming a sensor assembly, comprising:
forming a plurality of analyte sensors on a surface of a flexible substrate; forming a plurality of electrical contacts on the flexible substrate such that the electrical contacts are in electrical communication with a corresponding one of the analyte sensors; and configuring the flexible substrate to define a tube having an interior surface and an exterior surface with the surface on which the analyte sensors are formed defining the interior surface of the tube such that the analyte sensors are disposed on the interior surface of the tube, wherein the substrate is further configured to have a tab extending from the tube in a tangential relationship to the tube, wherein the at least one electrical contact is positioned on the tab.

12. The method of claim 11, wherein the tube is configured to have a circular cross-section.

13. The method of claim 11 further comprising the step of:
forming a plurality of amplifier front-end circuits on the substrate proximate to and in electrical communication with a corresponding one of the analyte sensors.

* * * * *